US00PP26548P2

(12) United States Plant Patent
Wood

(10) Patent No.: US PP26,548 P2
(45) Date of Patent: Mar. 29, 2016

(54) LILAC PLANT NAMED 'SMSXPM'

(50) Latin Name: *Syringa hybrida*
Varietal Denomination: SMSXPM

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 144 days.

(21) Appl. No.: 13/987,979

(22) Filed: Sep. 20, 2013

(51) Int. Cl.
*A01H 5/02* (2006.01)

(52) U.S. Cl.
USPC ..... Plt./248

(58) Field of Classification Search
USPC ..... Plt./248
See application file for complete search history.

(56) References Cited

PUBLICATIONS

Spring Meadow Nursery, Flowering Shrubs Spring Meadow Nursery, Inc. Starter Plants Catalog and Shrub Reference 2012-2013, pp. 1-3, 9, 17 and 70.*

* cited by examiner

*Primary Examiner* — June Hwu
(74) *Attorney, Agent, or Firm* — C. A. Whealy

(57) ABSTRACT

A new and distinct cultivar of Lilac plant named 'SMSXPM', characterized by its compact, upright to outwardly spreading and low mounding plant habit; vigorous growth habit; freely branching habit; freely flowering habit; dark pink-colored flower buds; large inflorescences with strongly fragrant intense light pink-colored flowers; long flowering period and remontant flowering habit; and good cold hardiness.

3 Drawing Sheets

Botanical designation: *Syringa hybrida.*
Cultivar denomination: 'SMSXPM'.

BACKGROUND OF THE INVENTION

The present invention relates to a new and distinct cultivar of Lilac plant, botanically known as *Syringa hybrida* and hereinafter referred to by the name 'SMSXPM'.

The new Lilac plant is a product of a planned breeding program conducted by the Inventor in Grand Haven, Mich. The objective of the breeding program is to create new compact Lilac plants with repeat flowering habit and unique flower colors.

The new Lilac plant originated from a cross-pollination conducted by the Inventor during the spring of 2004 of *Syringa hybrida* 'Josee', not patented, as the female, or seed, parent with *Syringa hybrida* 'Red Pixie', not patented, as the male, or pollen, parent. The new Lilac plant was discovered and selected by the Inventor as a single flowering plant from within the progeny of the stated cross-pollination in a controlled environment in Grand Haven, Mich. during the spring of 2006.

Asexual reproduction of the new Lilac plant by softwood cuttings in a controlled greenhouse environment in Grand Haven, Mich. since the spring of 2007 has shown that the unique features of this new Lilac plant are stable and reproduced true to type in successive generations of asexual reproduction.

SUMMARY OF THE INVENTION

Plants of the new Lilac have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SMSXPM'. These characteristics in combination distinguish 'SMSXPM' as a new and distinct Lilac plant:

1. Compact, upright to outwardly spreading and low mounding plant habit.
2. Vigorous growth habit.
3. Freely branching habit.
4. Freely flowering habit.
5. Dark pink-colored flower buds.
6. Large inflorescences with strongly fragrant intense light pink-colored flowers.
7. Long flowering period and remontant flowering habit.
8. Good cold hardiness.

Plants of the new Lilac can be compared to plants of the female parent, 'Josee'. Plants of the new Lilac differ primarily from plants of 'Josee' in the following characteristics:

1. Plants of the new Lilac are more compact than and not as upright as plants of 'Josee'.
2. Flowers of plants of the new Lilac are more fragrant than flowers of plants of 'Josee'.
3. Plants of the new Lilac and 'Josee' differ in flower color as plants of 'Josee' have lavender pink-colored flowers.

Plants of the new Lilac can be compared to plants of the male parent, 'Red Pixie'. Plants of the new Lilac differ primarily from plants of 'Red Pixie' in the following characteristics:

1. Plants of the new Lilac are more mounded than and not as upright as plants of 'Red Pixie'.
2. Plants of the new Lilac and 'Red Pixie' differ in flower color as plants of 'Red Pixie' have red purple-colored flowers.

Plants of the new Lilac can be also compared to plants of the *Syringa hybrida* 'Palibin', not patented. In side-by-side comparisons conducted in Grand Haven, Mich., plants of the new Lilac differed primarily from plants of 'Palibin' in the following characteristics:

1. Plants of the new Lilac and 'Palibin' differed in flower bud and flower color.
2. Flowers of plants of the new Lilac were not as fragrant as plants of 'Palibin'.
3. Plants of the new Lilac had a remontant flowering habit whereas plants of 'Palibin' only flowered once during the flowering season.

BRIEF DESCRIPTION OF THE PHOTOGRAPHS

The accompanying colored photographs illustrate the overall appearance of the new Lilac plant showing the colors as true as it is reasonably possible to obtain in colored reproductions of this type. Colors in the photographs may differ slightly from the color values cited in the detailed botanical description which accurately describe the colors of the new Lilac plant.

The photograph on the first sheet is a side perspective view of a flowering typical plant of 'SMSXPM' grown in a container.

The photograph on the second sheet is a side perspective view of a flowering typical plant of 'SMSXPM' grown in an outdoor nursery.

The photograph on the third sheet is a close-up view of a typical inflorescence of 'SMSXPM'.

DETAILED BOTANICAL DESCRIPTION

The aforementioned photographs and following observations, measurements and values describe plants grown during the spring and summer in six-gallon container and in ground beds in an outdoor nursery in Grand Haven, Mich. and under cultural practices typical of commercial production. Plants were six years old when the photographs and the description were taken. In the description, color references are made to The Royal Horticultural Society Colour Chart, 1995 Edition, except where general terms of ordinary dictionary significance are used.

Botanical classification: *Syringa hybrida* 'SMSXPM'.

Parentage:

*Female, or seed, parent.*—*Syringa hybrida* 'Josee', not patented.

*Male, or pollen, parent.*—*Syringa hybrida* 'Red Pixie', not patented.

Propagation:

*Type*.—By softwood cuttings.

*Time to initiate roots, summer*.—About 18 days at 27° C.

*Time to produce a rooted young plant, summer*.—About three months at 27° C.

*Root description*.—Fine, fibrous.

*Rooting habit*.—Freely branching; dense.

Plant description:

*Plant form and growth habit*.—Perennial shrub; compact, upright to outwardly spreading and low mounding plant habit; vigorous growth habit.

*Branching habit*.—Freely branching habit, about 47 lateral branches develop per plant.

*Plant height*.—About 82 cm.

*Plant diameter* (*area of spread*).—About 186 cm.

Lateral branch description:

*Length*.—About 45 cm.

*Diameter*.—About 2 mm.

*Internode length*.—About 3.5 cm.

*Aspect*.—Erect to about 10° from vertical.

*Texture*.—Smooth, glabrous.

*Color*.—Close to 200D.

Leaf description:

*Arrangement*.—Opposite, simple.

*Length*.—About 4.3 cm.

*Width*.—About 2.8 cm.

*Shape*.—Ovate.

*Apex*.—Acuminate.

*Base*.—Obtuse.

*Margin*.—Entire; slightly undulate and ciliate; no sinuses.

*Texture, upper and lower surfaces*.—Rugose, glabrous.

*Venation pattern*.—Pinnate.

*Color*.—Developing and fully expanded leaves, upper surface: Close to 147A; venation, close to 145A. Developing and fully expanded leaves, lower surface: Close to 147B; venation, close to 137C.

*Petioles*.—Length: About 1 cm. Diameter: About 1 mm. Texture, upper and lower surfaces: Smooth. Color, upper and lower surfaces: Close to 143C.

Flower description:

*Flower arrangement and flowering habit*.—Single salverform flowers arranged and axillary terminal panicles; inflorescences moderately dense to dense and conical in shape; freely flowering habit with usually about 75 flowers developing per inflorescence; flowers face upright to outwardly on inflorescences that may be upright, horizontal or downward depending on the inflorescences' position on the plant.

*Natural flowering season and flower longevity*.—Long flowering period; plants of the new Lilac flower during spring to autumn in Grand Haven, Mich.; remontant flowering habit; flowers last about three to four weeks on the plant; flowers not persistent.

*Fragrance*.—Strongly fragrant; fragrance sweet and pleasant.

*Inflorescence height*.—About 9 cm.

*Inflorescence diameter*.—About 4.7 cm.

*Flower diameter*.—About 1.2 cm.

*Flower length* (*height*).—About 1 cm.

*Flower buds*.—Length: About 5 mm. Diameter: About 2 mm. Shape: Obovate. Color: Close to 67C to 67D.

*Petals*.—Quantity and arrangement: Single whorl of four petals; lower portion of petals fused forming a narrow tube; corolla tube semi-erect to horizontal and occasionally recurved; corolla tube without undulations. Lobe length: About 7 mm. Lobe width: About 3 mm. Corolla tube length: About 1.2 cm to 1.5 cm. Corolla tube diameter: About 2 mm. Lobe shape: Elliptic. Apex: Cuspidate. Margin: Entire; apical margin initially moderately to strongly incurved and becoming flatter with development. Texture, upper and lower surfaces: Smooth, glabrous. Color: When opening, petal lobe upper surface: Close to 75B. When opening, petal lobe lower surface: Close to 73A. Fully opened, petal lobe upper and lower surfaces: Close to 76B. Corolla tube, inner and outer surfaces: Close to 73A to 73D.

*Sepals*.—Quantity and arrangement: Single whorl of five sepals; fused towards the base forming a campanulate-shaped calyx. Length: About 4 mm. Width: About 1 mm. Shape: Oblanceolate. Apex: Acute. Margin: Entire. Texture, upper and lower surfaces: Smooth. Color, upper and lower surfaces: Close to 138D becoming closer to 142C with development.

*Peduncles*.—Length: About 8.8 cm. Diameter: About 4.5 mm. Strength: Strong. Aspect: Erect to about 10° from lateral branch axis. Texture: Smooth. Color: Close to 137C.

*Pedicels*.—Length: About 6 mm. Diameter: About 1 mm. Strength: Strong. Aspect: About 40° to 50° from peduncle axis. Texture: Smooth. Color: Close to 137C.

*Reproductive organs*.—Androecium: Quantity of stamens per flower: About two. Anther shape: Oblong. Anther length: About 3 mm. Anther color: Close to 177A. Amount of pollen: None observed. Gynoecium: Pistil length: About 5 mm. Style length: About 3 mm. Style color: Close to 2D. Stigma shape: Round. Stigma color: Close to 2D. Ovary: Close to 143C.

*Fruits*.—Length: About 1.4 cm to 1.6 cm. Diameter: About 3 mm to 4 mm. Texture: Leathery. Color: Initially, close to 156B; with development becoming closer to 166A and eventually closer to 198B.

*Seeds*.—Length: About 9 mm. Diameter: About 2.5 mm. Color: Close to 165A.

Garden performance: Plants of the new Lilac have been observed to have good garden performance and to tolerate rain, wind and temperatures ranging from about −31° C. to about 38° C.

Pathogen & pest resistance: Plants of the new Lilac have been observed to be resistant to root rots common to Lilac plants. Plants of the new Lilac have not been shown to be resistant to pests and other pathogens common to Lilac plants.

It is claimed:

1. A new and distinct Lilac plant named 'SMSXPM' as illustrated and described.

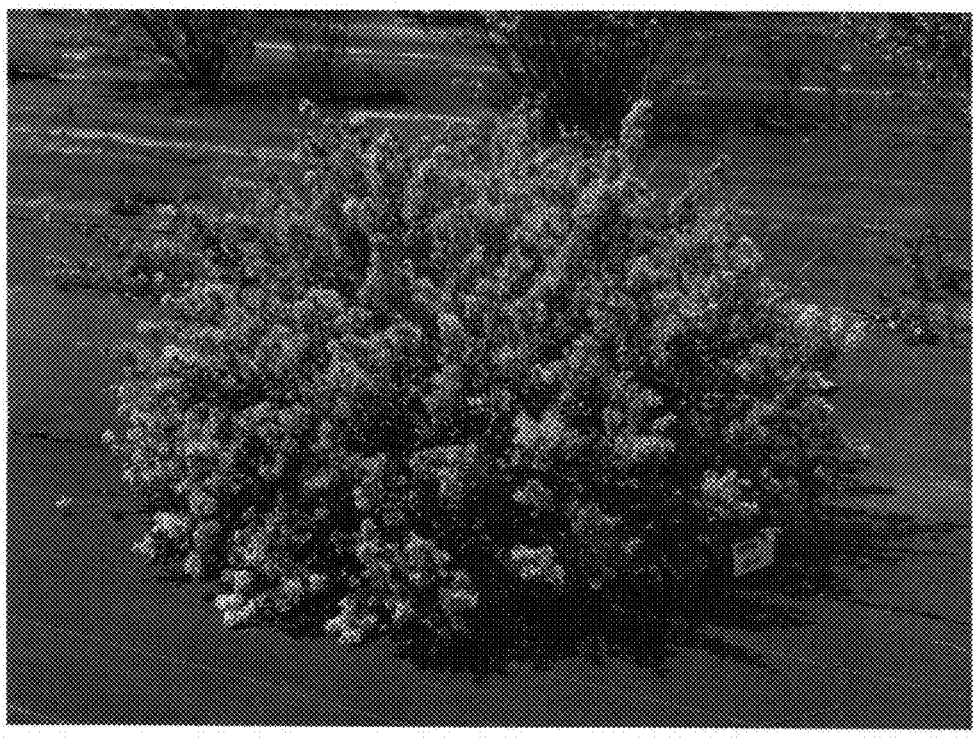

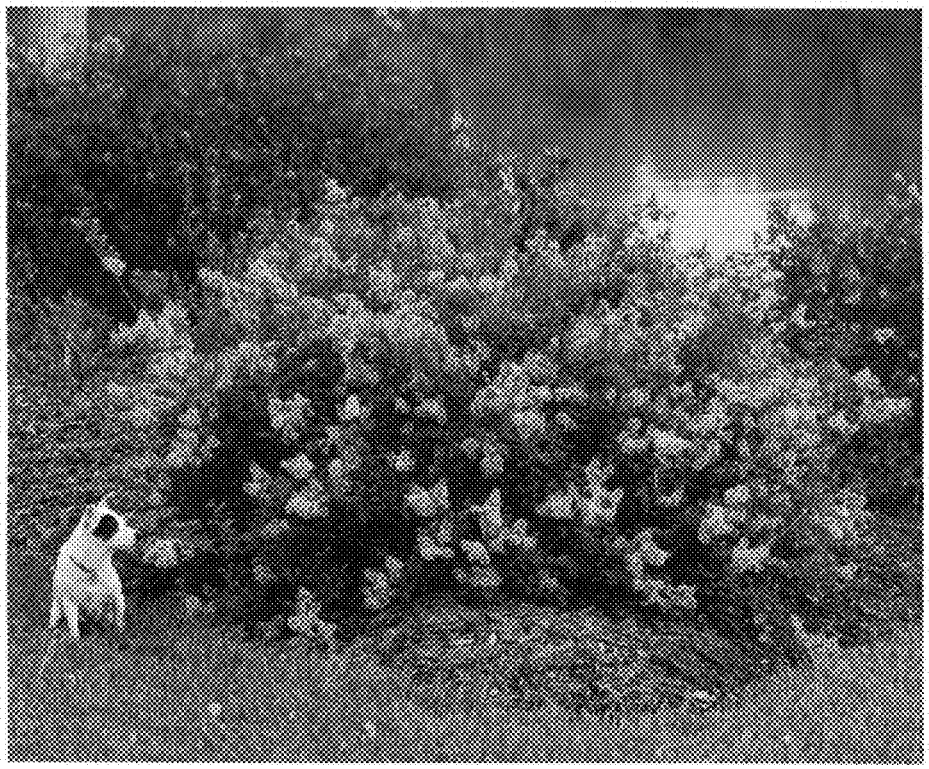

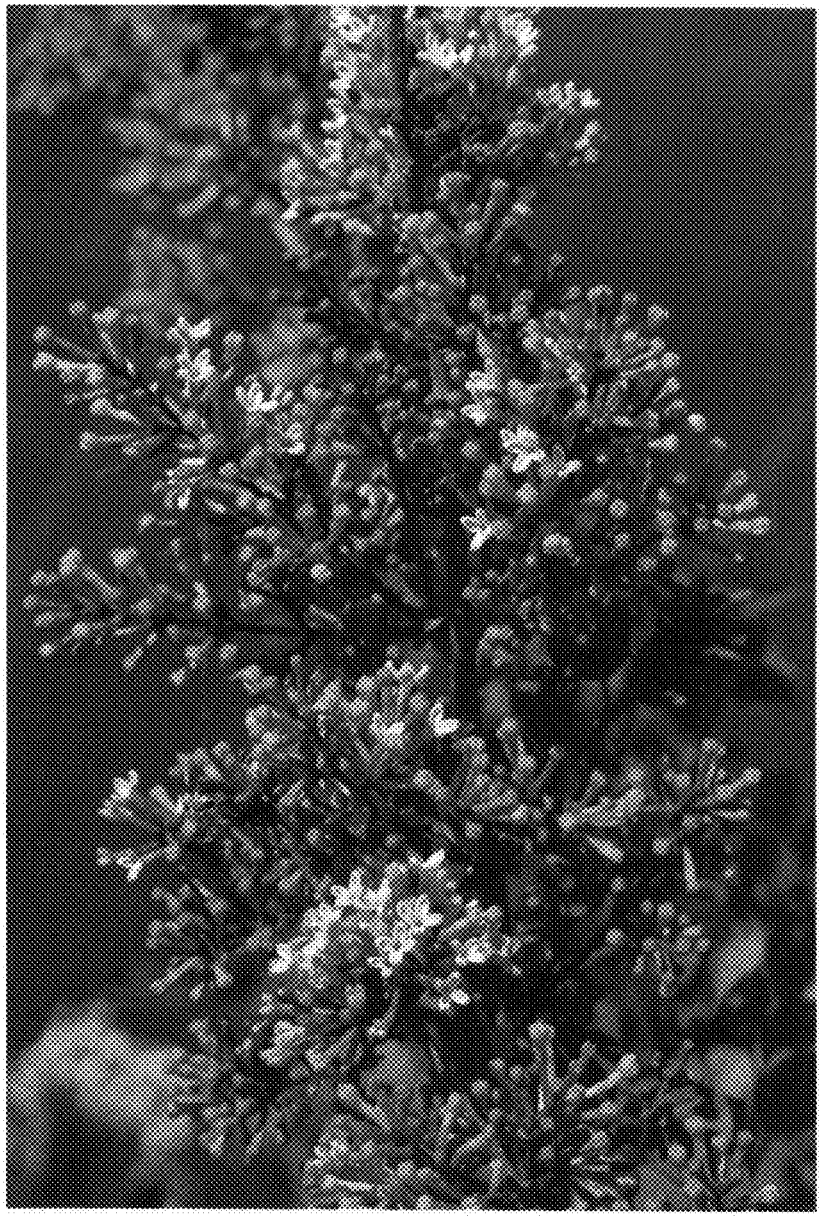

* * * * *